United States Patent
Leeds et al.

(10) Patent No.: US 6,393,100 B1
(45) Date of Patent: May 21, 2002

(54) ASYMMETRIC COLLIMATOR FOR CHEST OPTIMIZED IMAGING

(75) Inventors: Thomas M. Leeds, Pewaukee; Michael J. Pajerski, Oconomowoc, both of WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/475,854

(22) Filed: Dec. 30, 1999

Related U.S. Application Data

(60) Provisional application No. 60/162,543, filed on Oct. 29, 1999.

(51) Int. Cl.[7] .................................................. G21K 1/04
(52) U.S. Cl. ........................ 378/150; 378/147; 378/148; 378/160
(58) Field of Search ................................ 378/147, 148, 378/150, 160

(56) References Cited

U.S. PATENT DOCUMENTS 5,237,599 A * 8/1993 Gunji et al. ................. 378/148
6,208,712 B1 * 3/2001 Hernandez-Guerra ....... 378/150

* cited by examiner

Primary Examiner—Robert H. Kim
Assistant Examiner—Courtney Thomas
(74) Attorney, Agent, or Firm—Jenkens & Gilchrist

(57) ABSTRACT

Collimator apparatus is provided for an X-ray imaging system comprising an X-ray tube disposed to project an X-ray beam, and a detector spaced apart from the X-ray tube for receiving X-rays of the beam within an Active Imaging Area (AIA). The apparatus comprises a first collimator positioned along the path of the beam, the first collimator being vertically adjustable, and being operable to symmetrically collimate the beam. The apparatus further comprises a second collimating device positioned between the first collimator and the detector. The second collimating device limits the uppermost rays of the symmetrically collimated beam which reach the detector to a predetermined upper boundary. Thus, the second collimating device serves to fix the upper edge of the AIA on the detector. At the same time, the second collimating device allows the lowermost rays of the symmetrically collimated beam reaching the detector, which define the lower edge of the AIA, to have a lower boundary which is determined by selective adjustment of the first collimator.

14 Claims, 3 Drawing Sheets

ASYMMETRIC COLLIMATOR FOR CHEST OPTIMIZED IMAGING

This application claims the benefit of U.S. Provisional Application No. 60/162,543, filed Oct. 29, 1999.

BACKGROUND OF THE INVENTION

In a number of currently used X-ray imaging systems, such as a product of the General Electric Company known commercially as the Revolution XQ/i, an arrangement of adjustable collimator blades is provided to enable the field of view, or Active Imaging Area, to be symmetrically adjusted. As used herein, Active Imaging Area (AIA) refers to a rectangular area, at a specified distance from the tube of an X-ray imaging system, which receives incident X-rays projected by the tube. The dimensions of the AIA generally are adjustable to coincide with the dimensions of the detection area of an X-ray imaging medium, such as an X-ray film or a digital solid state X-ray detector, which is positioned to receive X-rays after projection through a patient or the like. Alternatively, the AIA may be adjusted to coincide with only a portion of the detection area of the medium.

In a symmetrically adjustable collimator, two pairs of spaced-apart collimator blades are mounted on the X-ray tube, one pair to adjust the vertical dimension (or length) of the AIA, and the other pair to adjust the horizontal dimension (or width) thereof. Thus, by rotating a small wheel or dial mounted on the collimator, the two collimator blades associated with the vertical dimension may be smoothly adjusted, to selectively increase or decrease such dimension. Assuming that the tube and detector are not manually positioned with respect to each other, this collimator adjustment is symmetric in that for any setting of the collimator blades, the distance or spacing between the focal spot center line and the top edge of the AIA will be equal to the spacing between the focal spot center line and the bottom edge of the AIA. The focal spot center line coincides with the axis of the projected X-ray beam.

Horizontal adjustment of the AIA is likewise symmetric, in that for any setting of the pair of collimator blades associated therewith, the spacings between the focal spot center line and the right and left edges of the AIA, respectively, will also be equal.

Symmetrically adjustable collimation, as described above, has been found to be very beneficial in an X-ray system. Such arrangement enables an X-ray technician or other user to position a patient in front of the X-ray detector, and to then quickly adjust dimensions of the X-ray beam as required for a particular patient and detector. Symmetric collimation is considered to be particularly useful in connection with digital solid-state X-ray detectors and with systems which utilize an auto tracking tube to enhance user productivity. In a system having the auto tracking tube feature, movement of the detector will result in an automatic corresponding movement of the X-ray tube, in order to maintain a prespecified relationship between the tube and detector. In an X-ray system such as the Revolution XQ/i, referred to above, the tube stand is provided with motorized travel, and automatically tracks the image center on the detector. This feature greatly enhances productivity in setting up an X-ray system for imaging, since a user only needs to manually position the detector with respect to a patient, and the tube will be positioned automatically. However, there is increasing interest in chest imaging, wherein the chin of a patient is positioned near the top of a detector, and the X-ray exposure is limited to the chest region and to the upper abdomen. At present, such imaging requires use of a lead shield or lead apron for the abdominal area, and manual positioning of the X-ray tube and the collimator. While an X-ray system with symmetric collimation may be adaptable for chest imaging, such adaptation may adversely affect image quality and user productivity, and may not take full advantage of auto tracking tube. In chest imaging it is desired to reduce the bottom or lower part of the AIA, without reducing the upper part thereof.

SUMMARY OF THE INVENTION

The invention is generally directed to collimator apparatus for an X-ray imaging system comprising an X-ray tube disposed to project an X-ray beam, and a detector which is spaced apart from the X-ray tube for receiving X-rays of the beam within an Active Imaging Area. The apparatus of the invention comprises a first collimator positioned along the path of the beam, the first collimator being vertically adjustable and operable to symmetrically collimate the beam. The apparatus further comprises a second collimating device positioned between the first collimator and the detector. The second collimating device is operable to limit the uppermost rays of the symmetrically collimated beam which reach the detector, and which thus define the upper edge of the AIA on the detector, to a predetermined upper boundary. At the same time, the second collimating device allows the lowermost rays of the symmetrically collimated beam reaching the detector, defining the lower edge of the AIA, to have a lower boundary which is determined by selective adjustment of the first collimator. Thus, the upper edge of the AIA on the detector is fixed, while the lower edge can be raised or lowered by means of the adjustable first collimator.

In a preferred embodiment of the invention, the second collimating device comprises a collimator blade fixably positioned to lie in the path of an upper portion of the symmetrically collimated beam, to prevent X-rays of the upper portion from reaching the detector. The first collimator comprises upper and lower vertically adjustable collimator blades, respectively positioned so that the beam passes therebetween The adjustable collimator blades are moved toward or away from each other, to vary the width of the collimated beam in a vertical plane, while the collimated beam remains vertically symmetrical. Preferably, the adjustable collimator blades are positioned within a housing, and the fixed collimator blade is fixably joined to the housing.

BRIEF DESCRIPTIONS OF THE DRAWINGS

DETAILED DESCRIPTION OF THE PREFERRED EMBODIMENT

Figure 1:
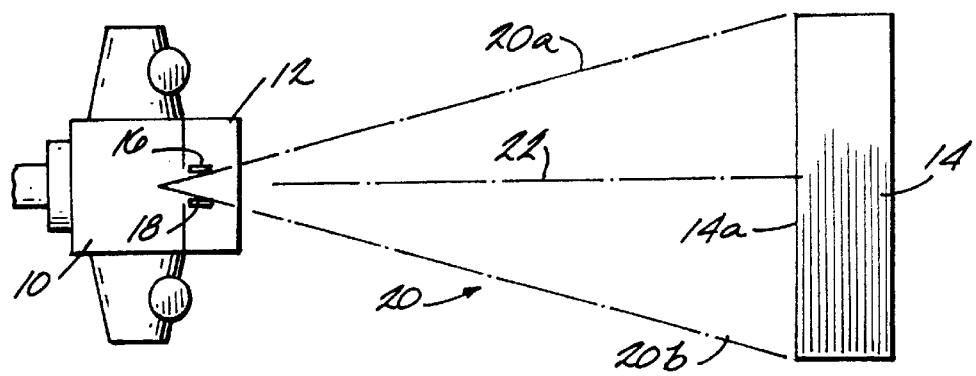
FIG. 1 is a schematic view showing an X-ray imaging system provided with a symmetric collimator.

In accordance with the invention, an X-ray system with symmetric collimation as described above may be readily modified for chest imaging, while minimizing the impact of the modification on the overall system architecture, and without losing important benefits and advantages of the system. Such modification is usefully understood by first referring to FIG. 1, which shows an X-ray tube 10 disposed to project a beam of X-rays through a collimator 12 adjacent thereto. The projected beam is incident upon the detector plane 14a of a digital solid-state X-ray detector 14, within an active imaging area or AIA. Collimator 12 is provided with internal collimator blades 16 and 18, which are movable toward or away from each other to respectively decrease or increase the vertical dimension of the AIA. FIG. 1 shows collimator blades 16 and 18 adjusted to provide an X-ray beam 20 bounded by an upper ray 20a and a lower ray 20b, which are directed to the upper and lower edges, respectively, of detector 14. Thus, collimator 12 in FIG. 1 provides a full field view, that is, the vertical dimension of beam 20 and the vertical dimension of detector plane 14a of detector 14 coincide at their intersection. In FIG. 1, internal collimator blades 16 and 18 provide symmetric collimation in that for any adjustment thereof, the X-ray beam projected therethrough will be symmetric about the focal point center line 22 of the beam.

Figure 2:
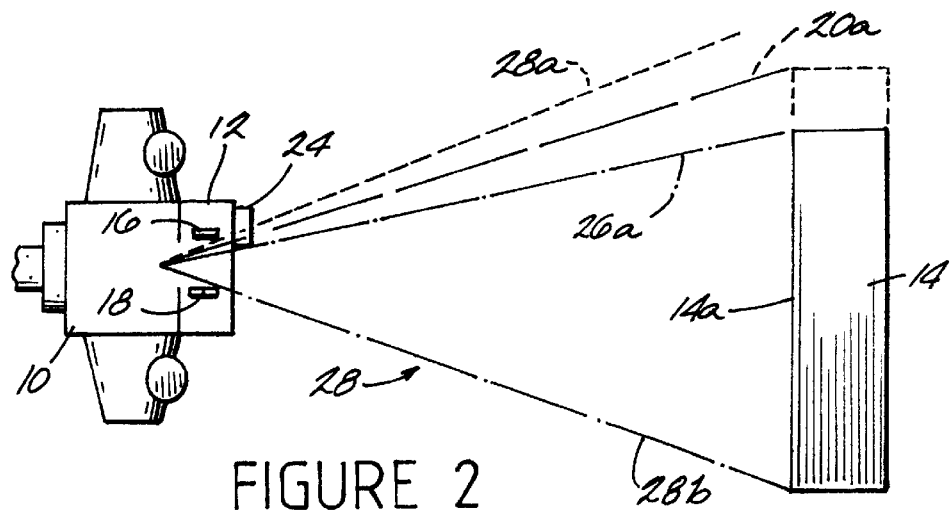
FIGS. 2 and 3 are schematic views showing an embodiment of the invention comprising a modification of the imaging system shown in FIG. 1.

Referring to FIG. 2, there is shown the arrangement depicted in FIG. 1, modified in accordance with the invention by joining a fixed collimator blade 24 to the collimator 12. More specifically, collimator blade 24 is fixably joined to collimator 12 so that it lies in the path of the upper portion of an X-ray beam projected out from collimator 12. Thus, upper ray 20a of beam 20 is blocked by collimator blade 24. As shown by FIG. 2, the uppermost portion of any beam which may be projected by collimator 12 is bounded by ray 26a.

As described hereinafter in connection with FIG. 4, detector 14 is vertically adjustable with respect to X-ray tube 10 and collimator 12. Accordingly, FIG. 2 further shows detector 14 vertically adjusted so that ray 26a of a projected beam intersects the upper edge of detector 14. To provide a full field of view on the detector plane 14a, so that the entire area of the detector plane may be used to acquire an image, collimator blades 16 and 18 are selectively moved apart, with respect to their positions as shown in FIG. 1, to provide an X-ray beam 28. Beam 28, which is wider than beam 20, has a lower ray 28b which intersects the lower edge of detector 14. However, upper ray 28a of beam 28 is blocked by the fixed collimator blade 24.

Figure 3:
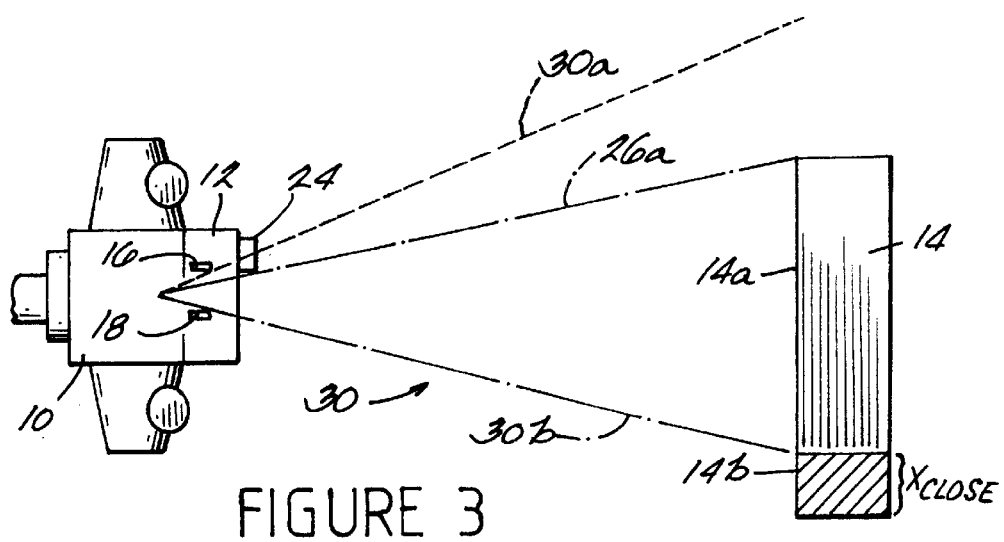

Referring to FIG. 3, there is shown collimator blades 16 and 18 moved toward one another, with respect to their positions shown in FIG. 2, to project an X-ray beam 30 having an upper ray 30a and a lower ray 30b. Upper ray 30a is blocked by fixed collimator blade 24, and ray 26a continues to intersect the upper edge of detector 14. However, ray 30b intersects the detector plane 14a at a distance $X_{close}$ above the lower edge thereof. Thus, a lower region 14b of detector 14 does not receive X-rays of beam 30. Moreover, the dimension $x_{close}$ of lower region 14b may be readily changed by adjustment of collimator blades 16 and 18, up to a limit described hereinafter, while the remainder of the detector continues to receive X-radiation. Accordingly, the collimator arrangement shown in FIGS. 2 and 3 is operable to asymmetrically collimate an X-ray beam projected therethrough.

Such arrangement may be readily employed for chest imaging as described above. A patient would be positioned directly in front of detector 14, with his or her chin near the top of the detector. Collimator blades 16 and 18 would then be adjusted to bring lower region 14b of detector 14 and the lower abdominal region of the patient, which is to be excluded from X-ray exposure, into coincident relationship. Thus, the arrangement of FIGS. 2 and 3 allows symmetric X-ray collimator 12 to be used in an application requiring asymmetric collimation, while at the same time maintaining image quality. In addition, the effective radiation received by a patient can be reduced without the use of cumbersome shields or aprons of the type described above. Moreover, in products such as the Revolution XQ/i, referred to above, a user will be able to position the patient in a customary manner utilizing the auto tracking tube designed for overall customer productivity.

Collimator 12 is also provided with a pair of internal collimator blades (not shown) which are used to adjust the horizontal dimension of the AIA. Though available, such collimator blades are generally not used in connection with the present embodiment of the invention.

Figure 5:
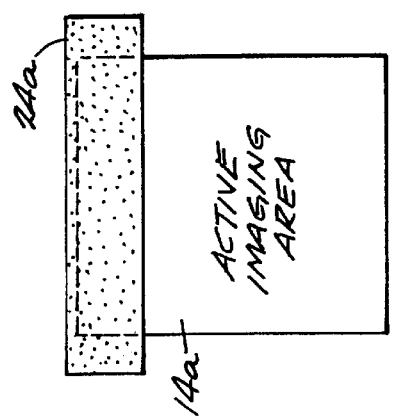
FIG. 5 is a view taken along lines 5—5 of FIG. 4.
Figure 4:
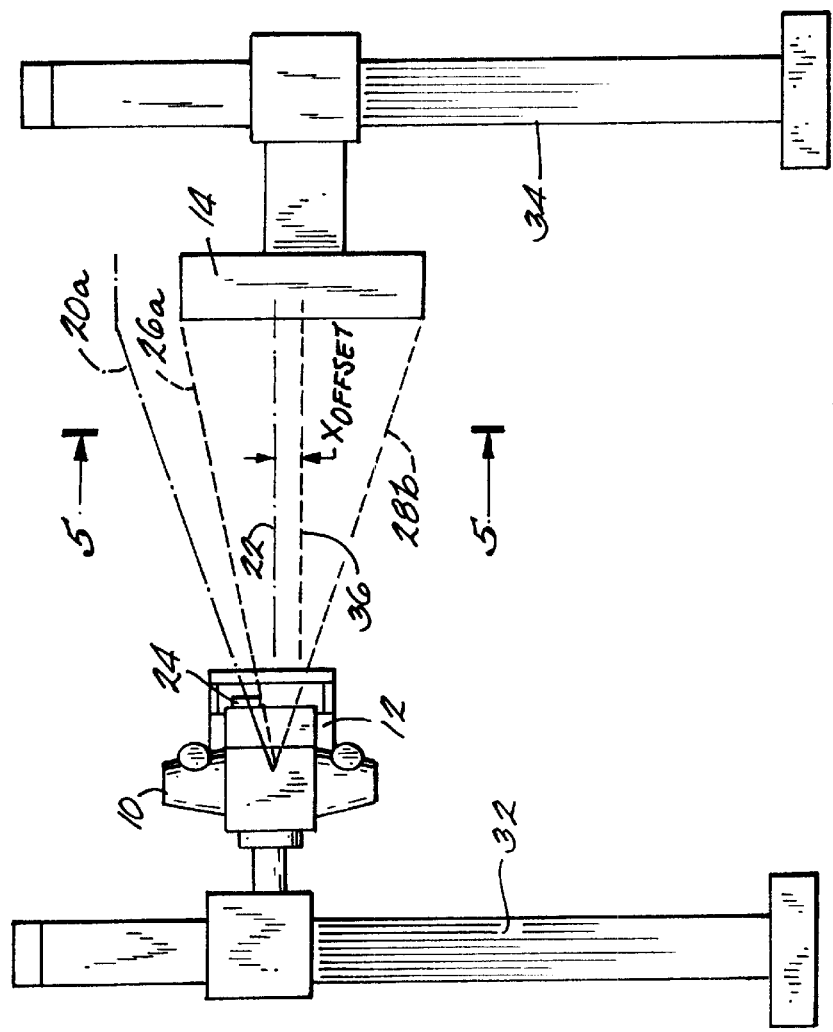
FIG. 4 shows the arrangement of FIG. 2 in greater detail.

Referring to FIG. 4, there is shown tube 10 and collimator 12 mounted for selected vertical positioning along a support column 32. Detector 14 is likewise shown to be mounted for vertical positioning along a support column 34. There is further shown collimator 12 adjusted as previously described in connection with FIG. 2, so that the X-ray system of FIG. 4 is set up for full field of view operation. That is, the AIA coincides with the entire detector plane 14a of detector 14. This is illustrated by FIG. 5. which also depicts a region 24a directly above detector 14. Region 24a represents an area from which X-rays projected by tube 10 are blocked by the action of fixed blade 24. Referring further to FIG. 4, there is shown the center line 36 of detector 14 offset from focal spot center line 22 of the X-ray tube 10 by an amount $X_{offset}$, due to the effect of fixed collimator blade 24.

Figure 7:
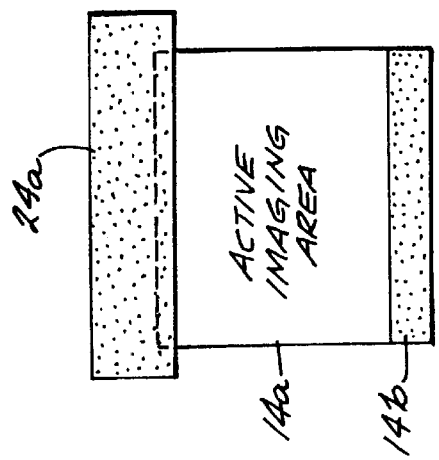
FIG. 7 is a view taken along lines 7—7 of FIG. 6.
Figure 6:
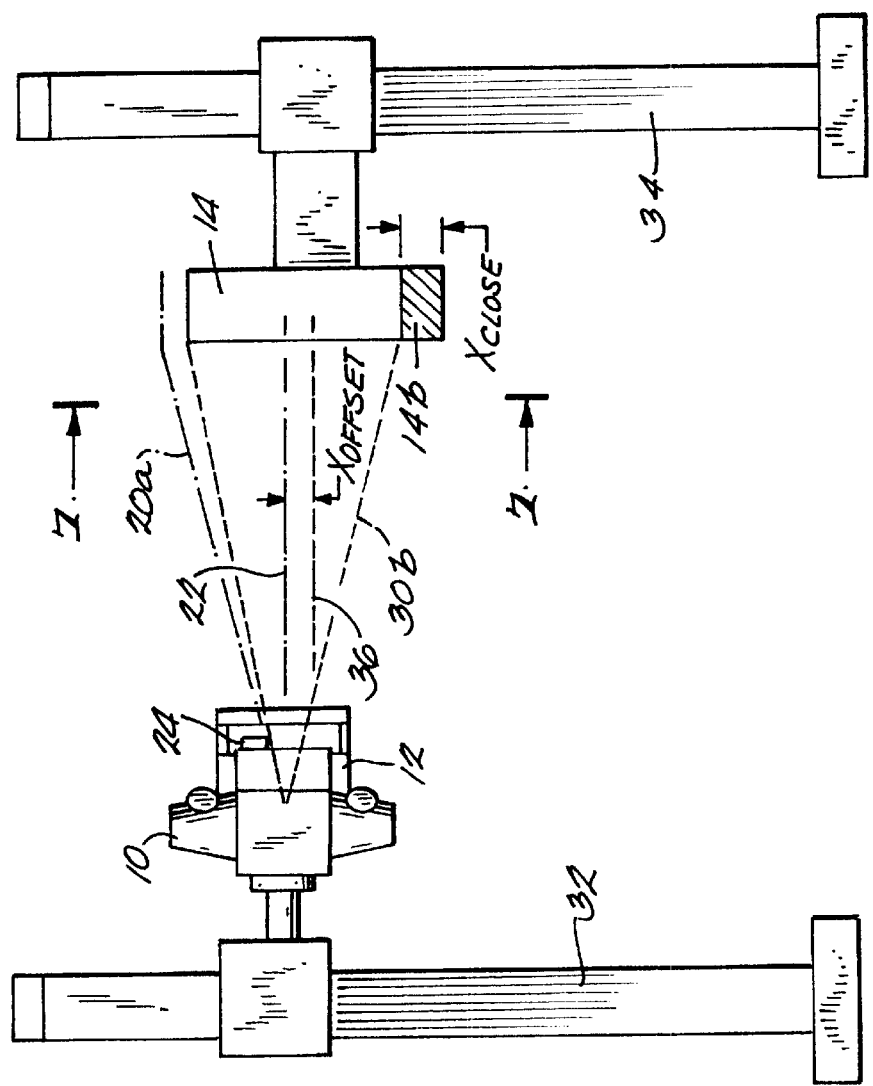
FIG. 6 shows the arrangement of FIG. 3 in greater detail.

Referring to FIG. 6, there is shown collimator 12 adjusted as previously described in connection with FIG. 3. Thus, the AIA on detector 14 is reduced by lower region 14b of length $X_{close}$, as described above and as illustrated by FIG. 7. As collimator blades 16 and 1 8 are moved closer together, the X-ray field of view on detector 14 will continue to close from the bottom of the detector upward, until $X_{close}=2X_{offset}$. At this point the field of view will converge together from the top and bottom of detector 14 at an equal rate, until the collimator blades 16 and 18 close together at focal spot center line 22.

Obviously, many other modifications and variations of the present invention are possible in light of the above teachings. It is therefore to be understood that within the scope of the disclosed concept, the invention may be practiced otherwise than as has been specifically described.

What is claimed is:

1. In an X-ray imaging system comprising an X-ray tube disposed to project an X-ray beam, and a detector spaced apart from said X-ray tube for receiving X-rays of said beam within an Active Imaging Area, collimator apparatus comprising:

a first collimator positioned along the path of said beam, said first collimator being adjustable and operable to symmetrically collimate said beam for any adjustment of said collimator; and a second collimating device comprising a collimator blade fixably positioned to lie in the path of a portion of said symmetrically collimated beam to limit first selected rays of said symmetrically collimated beam reaching said detector to a nonadjustable first boundary, defining a first edge of said Active Imaging Area, while allowing second selected rays of said symmetrically collimated beam reaching said detector to define a second edge of said Active Imaging Area which is in parallel spaced relationship with said first edge, and which is determined by selective adjustment of said first collimator.

2. The apparatus of claim 1 wherein:

said first collimator comprises two adjustable collimator blades respectively positioned so that said beam passes therebetween.

3. The apparatus of claim 2 wherein:

said collimator blades of said first collimator are adjustable to vary the width of said collimated beam in a vertical plane, while said collimated beam remains vertically symmetrical.

4. The apparatus of claim 2 wherein:

said X-ray tube and said detector are respectively mounted to enable vertical movement therebetween, in order to selectively position said detector in relation to said upper and lower boundaries of said rays reaching said detector, said upper and lower boundaries comprising the upper and lower edges, respectively, of said Active Imaging Area.

5. An X-ray imaging system comprising:

an X-ray tube disposed to protect an X-ray beam having a center line;

a detector spaced apart from said X-ray tube for receiving X-rays of said beam within an Active Imaging Area;

an adjustable first collimator means positioned along the path of said beam for collimating said beam so that said collimated beam is symmetrical with respect to said center line, in a specified plane, for any adjustment of said first collimator means; and a second collimator means, comprising a collimator blade fixably positioned to lie in the path of a portion of said symmetrically collimated beam, for limiting first selected rays of said symmetrically collimated beam reaching said detector to a nonadjustable first boundary defining a first edge of said Active Imaging Area, said fixably positioned collimator blade allowing second selected rays of said collimated beam reaching said detector to define a second edge of said Active Imaging Area which is in parallel, spaced relationship with said first edge.

6. The apparatus of claim 5 wherein:

said first collimator means comprises a pair of collimator blades which are adjustable to vary the width of said collimated beam in a vertical plane, while said collimated beam remains vertically symmetrical.

7. The apparatus of claim 6 wherein:

said fixably positioned collimator blade lies in the path of an upper portion of said symmetrically collimated beam, to prevent X-rays of said upper portion from reaching said detector.

8. The apparatus of claim 7 wherein:

said X-ray tube and said detector are respectively mounted to enable vertical movement therebetween, in order to selectively position said detector in relation to said first and second edges, which comprise upper and lower edges, respectively, of said Active Imaging Area.

9. In an arrangement comprising an X-ray tube disposed to project an X-ray beam having a center-line towards a detector spaced apart therefrom, in order to receive X-rays on the detector within an Active Imaging Area, a method for adjusting edges of the Active Imaging Area comprising the steps of:

performing a first collimating operation on said projected beam to apply a first upper boundary and a first lower boundary to said beam, said first upper and lower boundaries being selectively adjustable; and performing a second collimating operation on said projected beam to apply a nonadjustable second upper boundary to said beam, said nonadjustable upper boundary determining the upper edge of said Active Imaging Area, and said adjustable first lower boundary determining the lower edge of said Active Imaging Area.

10. The method of claim 9 wherein:

said first upper boundary and said first lower boundary are symmetrical to each other, with respect to said center line of said beam, for any adjustment of said first upper and lower boundaries.

11. The method of claim 10 wherein:

said X-ray tube and said detector are respectively mounted to enable vertical movement therebetween.

12. The method of claim 11 wherein:

said method includes the step of establishing said vertical movement between said X-ray tube and said detector in order to bring the upper edge of said Active Imaging Area and the upper edge of said detector into substantial alignment with each other.

13. The method of claim 12 wherein said method includes the steps of:

placing a patient between said tube and said detector so that the upper edge of said Active Imaging Area is proximate to the chest region of said patient; and adjusting said first lower boundary of said beam to position the lower edge of said Active Imaging Area above the abdominal region of said patient.

14. The method of claim 13 wherein:

said X-ray tube is disposed to move vertically, in response to movement of said detector, to maintain a specified relationship between said center line of said beam and a center point on said detector.

* * * * *